(12) United States Patent
Wich-Heiter

(10) Patent No.: US 9,028,439 B2
(45) Date of Patent: May 12, 2015

(54) METHOD FOR PREPARING A TREATMENT MACHINE AND TREATMENT MACHINE

(75) Inventor: Joachim Wich-Heiter, Wuerzburg (DE)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 1470 days.

(21) Appl. No.: 12/450,914

(22) PCT Filed: Apr. 11, 2008

(86) PCT No.: PCT/EP2008/002896
§ 371 (c)(1),
(2), (4) Date: Oct. 19, 2009

(87) PCT Pub. No.: WO2008/128664
PCT Pub. Date: Oct. 30, 2008

(65) Prior Publication Data
US 2010/0100034 A1 Apr. 22, 2010

(30) Foreign Application Priority Data
Apr. 18, 2007 (DE) .................. 10 2007 018 362

(51) Int. Cl.
A61M 1/00 (2006.01)
A61M 1/28 (2006.01)
A61M 1/14 (2006.01)
A61M 5/44 (2006.01)

(52) U.S. Cl.
CPC . A61M 1/28 (2013.01); A61M 1/14 (2013.01); A61M 5/44 (2013.01); A61M 2205/127 (2013.01); A61M 2205/128 (2013.01)

(58) Field of Classification Search
USPC ........... 604/29, 131–133, 246–256, 500, 505, 604/508, 513, 518, 519, 520
See application file for complete search history.

(56) References Cited

U.S. PATENT DOCUMENTS 5,324,422 A * 6/1994 Colleran et al. ................ 210/85
2004/0009254 A1 1/2004 Eloo et al.

FOREIGN PATENT DOCUMENTS

EP 0 815 882 A2 7/1998
WO WO 2005/042065 A2 5/2005

* cited by examiner

Primary Examiner — Kevin C Sirmons
Assistant Examiner — Phillip Gray
(74) Attorney, Agent, or Firm — Jacobson Holman, PLLC

(57) ABSTRACT

The present invention relates to a method for the preparation of a treatment machine for the treatment of a medical liquid comprising a coupling surface with actuators, with a cassette comprising a hard part with liquid-conducting passages which are covered by a flexible film being able to be coupled to the coupling surface of the treatment machine so that the actuators can control the liquid flow in the liquid-conducting passages by pressing the flexible film down into the cassette. In this connection, a switch is made after the setting up of the treatment machine and before the start of treatment into a stand-by mode in which the actuators are alternately moved to relieve the flexible film. It is possible for the first time by the stand-by mode before the start of treatment in accordance with the invention to completely uncouple the time-consuming setting up of the treatment machine from the treatment itself in a time aspect. The present invention furthermore comprises a corresponding treatment machine having a control for the carrying out of the method in accordance with the invention.

14 Claims, 4 Drawing Sheets

Legend

1. Treatment cycle
2. Inflow volume
3. Dwell time
4. Outflow volume
5. Initial outflow
6. Last inflow

METHOD FOR PREPARING A TREATMENT MACHINE AND TREATMENT MACHINE

This is a national stage of PCT/EP08/002896 filed Apr. 11, 2008 and published in German, which has a priority of German no. 10 2007 018 362.5 filed Apr. 18, 2007, hereby incorporated by reference.

BACKGROUND OF THE INVENTION

The present invention relates to a method for the preparation of a treatment machine for the treatment of a medical liquid comprising a coupling surface with actuators, with a cassette comprising a hard part with liquid conducting passages which are covered by a flexible film being able to be coupled to the coupling surface of the treatment machine so that the actuators can control the liquid flow in the liquid conducting passages by pressing the flexible film down into the cassette. The present invention furthermore comprises a corresponding treatment machine having a control for the carrying out of the method in accordance with the invention. The treatment machine in accordance with the invention is in particular a treatment machine for dialysis, in particular for peritoneal dialysis.

When setting up such a treatment machine, the required cassette, which is configured as a disposable article, has to be inserted into the machine and coupled to the coupling surface. For this purpose, the disposable cassette has a coupling plane for the coupling to the coupling surface of the treatment machine which is areally closed with a thin flexible polymer film so that different actuators and sensors of the treatment machine can couple to the outer film surface. The actuators can be valve tappets. The valve tappets press the flexible polymer film at different points into corresponding liquid conducting passages or recesses of the cassette and thus seal the liquid conducting passages.

For technical material and hygienic reasons it has previously not been possible to allow such a treatment machine, and indeed in particular a machine for automated peritoneal dialysis (APD), to be left in a waiting mode with an inserted cassette after the setting up. The spring-loaded valve tappets can cause a visco-elastic deformation (creep deformation) of the film, so-called sack formation, on a permanent pressure effect of the tappet onto the disposable film. Such a sack formation must, however, be avoided because otherwise the functional capability of the disposable cassette or of the valves formed by the actuators in interaction with the film can be impaired. Peritoneal dialysis patients who are treated by means of home peritoneal dialysis must therefore accept restrictions in their freedom of mobility in accordance with the methods known from the prior art because they are forced to start the treatment which lasts several hours immediately after the preparation (setting up) of the dialysis machine. This is generally accepted as inevitable by the patients and is not further questioned.

It is admittedly known that a first cycle of outflow and inflow can be carried out during the day and the automated peritoneal dialysis treatment can then be interrupted. The problem described above of material creep of the film also occurs in such a case. A regular movement of the valve tappets is automatically carried out in accordance with a specific logic during the interruption mode as a counter-measure against the creep deformation of the disposable film. It is prevented by this movement that the film deforms at the valve points due to a permanent pressure effect of the tappet. The additional cycle during the day admittedly improves the efficiency of the peritoneal dialysis, but further restricts the patient in his daily agenda.

With known treatment units, the treatment must in particular always be started immediately after the setting up of the treatment machine. The setting up of the dialyzer is, however, relatively time consuming and complex and comprises the steps of system check, inserting the cassette, inserting the solution bag connectors, connecting the drainage line, filling the cassette and the tubes. It would therefore be desirable for the improvement of the quality of life of the patient to design the procedures more flexibly and to reduce the restriction in the freedom of movement of the patient to the absolutely required amount so that the patient can participate in social life more flexibly.

SUMMARY OF THE INVENTION

It is therefore the object of the present invention to provide a method for the preparation of a treatment machine as well as a corresponding treatment machine which permit a more flexible design of the procedures in the preparation of the treatment machine.

This object is solved in accordance with the invention by a method for the preparation of a treatment machine in accordance with claim 1. In this connection, a switch is made after the setting up of the treatment machine and before the start of treatment into a stand-by mode in which the actuators are alternately moved to relieve the flexible film. It is possible for the first time by the stand-by mode before the start of treatment in accordance with the invention to completely uncouple the time-consuming setting up of the treatment machine from the treatment itself in a time aspect. Unlike treatment machines in accordance with the prior art in which an interruption between the setup and the treatment was even explicitly prohibited and this restriction in the patient's freedom of movement was accepted as inevitable, a substantial flexibilization of the procedure is now possible. It is possible by the movement of the valve tappet also to maintain the stand-by mode over very long time periods without having to fear a creep deformation of the film due to a permanent pressure effect of the actuators.

Whereas in accordance with the prior it was not only considered inevitable, but actually sensible to start the treatment immediately subsequently to the setting up in order not to prolong the total duration by additional waiting times, the setup and the treatment can for the first time be completely uncoupled from one another due to the stand-by mode in accordance with the invention, which permits a substantial relief for the patient in the design of their daily procedure. It is in particular the very long stand-by times which are possible with the method in accordance with the invention which make a stand-by mode before the treatment sensible at all. A demand for longer stand-by times between setup and start of treatment did not even exist at all in contrast in the prior art since the patient actually wanted to take the treatment as fast as possible. Advantageously, in contrast, the stand-by mode is maintained in the present invention for 10 hours, further advantageously for 15 hours.

With the help of the present invention, for example, the patient can set up the treatment machine at some time during the day and put it into stand-by mode, e.g. take part in social life in the evening, and connect immediately at the start of the night treatment without any further time-consuming preparations and start the night treatment. The treatment is then carried out automatically during sleep in the known manner.

The actuators are advantageously moved in the stand-by mode so that no previously closed flow paths are opened. The fluid connections within the cassette are thus substantially not changed during the stand-by mode, but the creep deformation of the film is effectively prevented by an alternating use of e.g. adjacent valve tappets.

Further advantageously, the actuators are moved at regular intervals, further advantageously at intervals of 5 to 20 minutes. A reliable prevention of a creep deformation is hereby ensured, with this stand-by mode also being able to be maintained over long waiting periods without damaging the film.

The present invention further includes a method for the preparation of a treatment machine for the treatment of a medical liquid, with a switch being made after the setting up of the treatment machine and before the start of treatment into a stand-by mode in which an overpressure is established in the system. Since an overpressure is established in the cassette in accordance with the invention during the stand-by mode, contamination over the connected connectors is effectively prevented. It is evident that such a prevention of contamination is of great advantage independently of the movement of the actuators in accordance with the invention. However, in particular a combination of both methods is advantageous in a particular manner since hereby very long stand-by times are also reliably made possible.

The present invention further comprises treatment machines whose control is configured for the carrying out of the methods in accordance with the invention. The present invention therefore furthermore includes a treatment machine for the treatment of a medical liquid comprising a coupling surface with actuators and with a control, with a cassette comprising a hard part with liquid conducting passages which are covered by a flexible film being able to be coupled to the coupling surface of the treatment machine so that the actuators can control the liquid flow in the liquid conducting passages by pressing the flexible film down into the cassette. In accordance with the invention, the control of the treatment machine has a stand-by mode which can be switched on after the setting up of the treatment machine and before the start of treatment in which the actuators are alternately moved to relieve the flexible film. The advantages already described with reference to the method are hereby provided. It is thus in particular possible to put the set-up dialysis machine into a state before the first patient connection which makes it possible to connect the patient only hours later and then to be able to start the treatment directly. During this stand-by mode before the start of treatment, the counter-measures already described above with respect to the sack formation in the film are carried out.

The actuators are in particular advantageously moved in the stand-by mode such that no previously closed flow paths are opened. Further advantageously, the actuators are moved in the stand-by mode at regular intervals, advantageously at intervals of 5 to 20 minutes.

Further advantageously, the present invention also comprises a treatment machine in which counter-measures against contamination of the cassette are carried out during the stand-by mode. For this purpose, the present invention in particular includes a treatment machine in which the control has a stand-by mode which can be switched on after the setting up of the treatment machine and before the start of treatment and in which the control establishes an overpressure in the system. As in the method in accordance with the invention, a contamination of the set is hereby in turn effectively prevented. In turn, such a treatment machine can be of great advantage independently of the movement of the actuators during the stand-by mode, with in particular a combination of both control features, however, being of particular advantage.

Further advantageously, the control of the treatment machine in accordance with the invention switches automatically into the stand-by mode after the setting up. The control in particular switches into the stand-by mode if the treatment is not started within a predetermined time. It is hereby ensured that the counter-measures with respect to sack formation and contamination are carried out if the treatment is not started. The automatic switching into the stand-by mode ensures that operating errors by the patient cannot occur at all.

Further advantageously, the treatment machine in accordance with the invention is a treatment machine for peritoneal dialysis, in particular a treatment machine for automatic peritoneal dialysis.

The present invention will now be presented in more detail with reference to an embodiment and to drawings.

BRIEF DESCRIPTION OF THE DRAWINGS

There are shown
FIG. 1 a disposable cassette.

DESCRIPTION OF THE PREFERRED EMBODIMENTS

In the present invention, both the setting up of the treatment machine and the treatment of the patient are carried out as with treatment machines of the prior art, with it now being possible for the first time, however, due to the stand-by mode in accordance with the invention to uncouple both processes in time.

Figure 1:
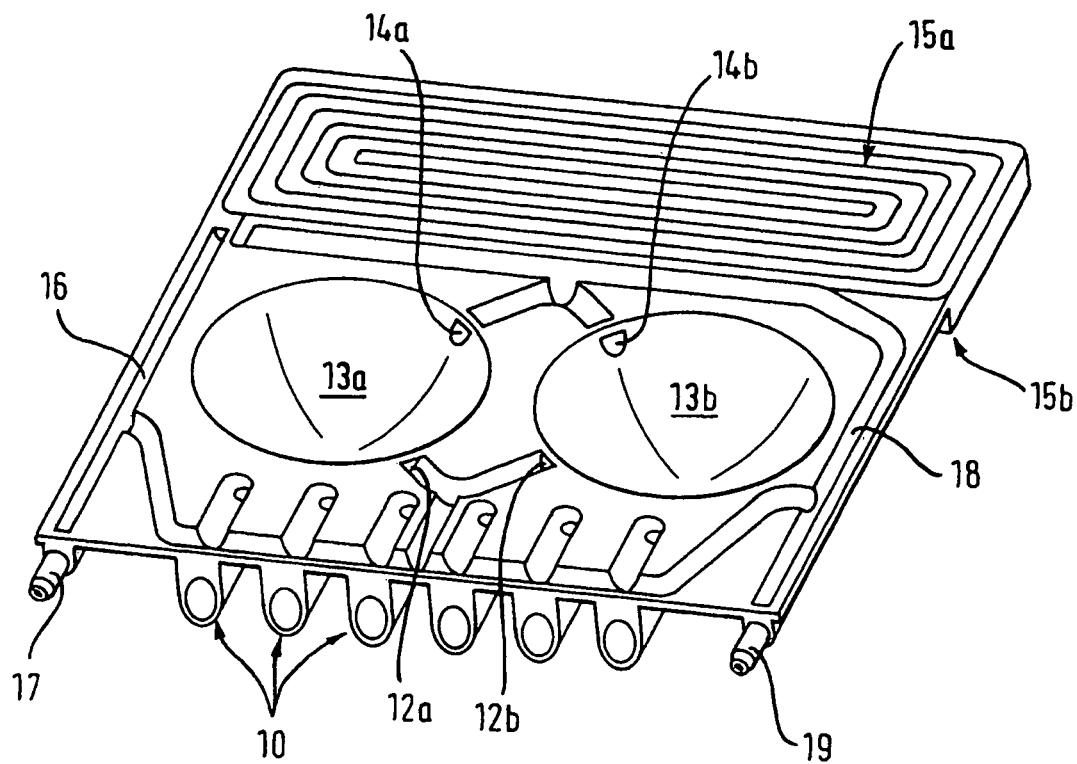

In FIG. 1, the cassette is now first shown which is used both in known treatment machines and in the present invention and comprises a hard part with liquid conducting passages which are covered from a flexible film which is not shown. At the left or at the right at the front, the cassette has a connector 17 for the patient hose as well as a connector 19 for the drainage hose. Set stubs 10 for the connection of solution bags are located therebetween. The cassette has passages 18 for the dialysate of the patient as well as passages 16 for the dialysis liquid to the patient.

The liquid is pumped via a left pump chamber 13a and a right pump chamber 13b which are configured as semi-spherical like recesses in the hard part. The pump chambers 13a and 13b each have inlets 12a and 12b as well as outlets 14a and 14b. Furthermore, an upper continuous flow heating region 15a and a lower continuous flow heating region 15b are provided in the cassette and the dialysis liquid which flows through is in contact in them with corresponding heating elements of the treatment machine and is heated to body temperature. The hard part of the cassette with the liquid conducting passages and the semi-spherical like pump chambers 13a and 13b is covered by a transparent and heat conductive flexible film.

A continuous pumping is realized by the reciprocal pressing of the pump pistons on the coupling surface of the treatment machine, by which the film is pressed into the pump chambers 13a and 13b. The passageways are controlled by valves whose valve tappets press the flexible film into the corresponding flow passages and recesses and cassette and so close the flow paths in the cassette. Different flow paths for the dialysis liquid can hereby be realized, with the dialysis liquid being able to be pumped e.g. out of the connected solution bags into the patient line.

The required steps for the setting up of the treatment machine will now be described with which the patient has to prepare the treatment machine after the switching on, with him/her being guided by a screen display. In the first step, a sterile set with a disposable cassette is placed into the unit. Then solvent bags with the dialysis liquid are connected to the cassette. For this purpose, the connectors of the solution bags are inserted into a drawer and are later pushed by a connector rail of the drawer onto the cylindrical set stubs 10 of the cassette. The set stubs are hereby pierced by the connectors and a fluid communication is established between the solvent bag and the cassette. The drainage line now has to be connected to the set and the set and the hoses have to be filled. Only now has the dialyzer been set up so that the patient can be connected by unscrewing a protective cap from the patient connector and screwing on a catheter extension. The liquid conducting passages in the cassette are now closed via valve tappets in order to prevent an unwanted flow through the cassette.

Figure 2C:
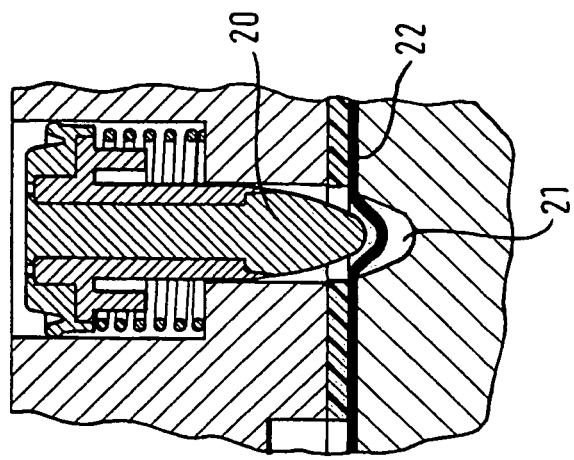
FIGS. 2a to 2c the sack formation on the closing of the liquid conducting passages of the cassette by a permanent effect of the actuators.
Figure 2B:
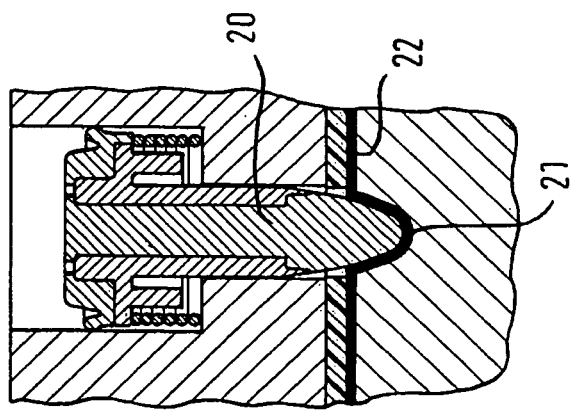

In this connection, the valve tappets may not act on the film without interruption for a longer period since otherwise an unwanted creep deformation of the film starts. It is shown in FIGS. 2a to 2c how an actuator 20 on the machine side in the form of a valve tappet presses the film 22 into the liquid conducting passage 21 and effects such a creep deformation.

Figure 2A:
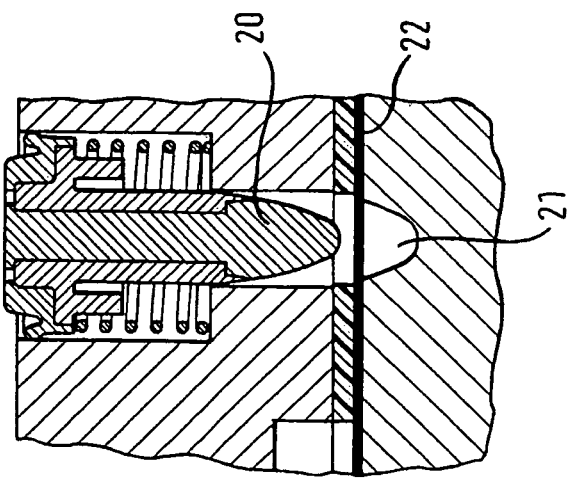

In FIG. 2a, the valve is in the totally open state in which the valve tappet 20 is not in contact with the film 22. Said film is pressed with sealing regions of the hard part in addition to the liquid conducting passage 21 and extends in a planar manner above the liquid conducting passage 21. In FIG. 2b, the valve tappet 20 is now completely pressed into the liquid conducting passage 21 so that the film 22 undergoes maximum deformation and the liquid conducting passage 21 is closed. If the valve tappet 20 is relieved again after a longer strain period, the deformation is maintained up to a specific degree, as is shown in FIG. 2c. Since the deformed film 22 has a shape similar to a sack at this point, one talks of sack formation here. The longer the tappet 20 presses into the film 22, the more permanent the deformation or sack formation can be.

The suction or pressure arising due to the flow in the liquid conducting passage 21 can force the film sack into the passage when the valve is opened such that a restriction or even a closure can occur. Too long a deformation of the film 22 by the valve tappets 20 with accompanying sack formation can thus impair the functional capability of the cassette or even completely preclude a proper functioning. In devices in accordance with the prior art, the treatment must be started immediately after the end of the filling procedure.

So that the set-up unit can also remain in the set-up state for a longer time, so that the treatment does not have to be started immediately after the setting up, the stand-by mode in accordance with the invention is provided, during which the valve tappets are moved regularly in order to relieve the flexible film and so to counter sack formation. It can be prevented by this reduction of the permanent effective period of the valve tappet that a permanent deformation of the set film occurs.

Figure 3A:
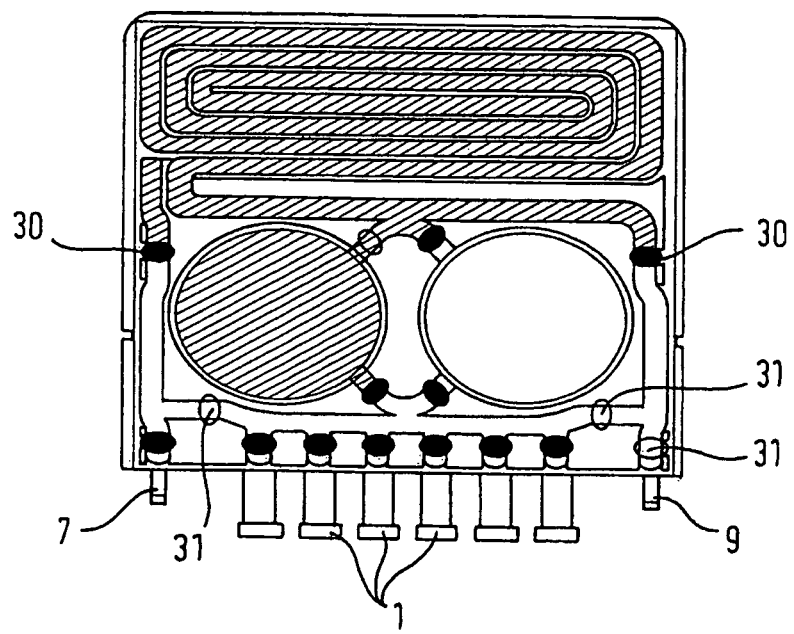
FIGS. 3a and 3b different valve tappet positions during the stand-by mode in accordance with the present invention.
Figure 3B:
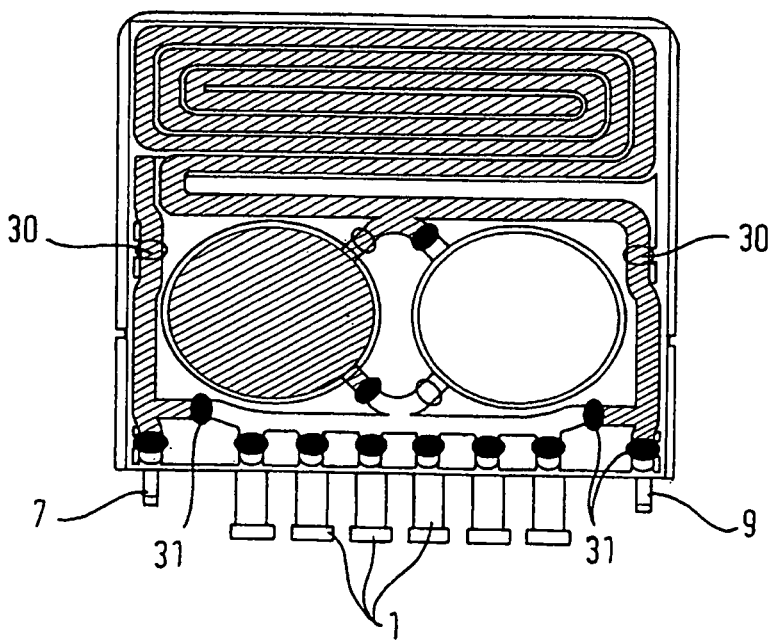

As shown with reference to FIGS. 3a and 3b, different valve tappet positions can be used by using valve tappets which are not required for the control of the active flow path without the effective flow path between the outer connectors varying. In this connection, the valve tappets can be removed from the set film after a fixed time interval, e.g. 10 minutes, and replaced by other valve tappets.

FIGS. 3a and 3b show by way of example two different valve tappet positions, with the regions of the cassette in fluid communication with one another each being shown hatched or white. In FIG. 3a, the valves 30 are closed, whereas the valves 31 are open. In FIG. 3a, the valve tappets of the valves 30 are therefore pressed down into the film, whereas the valve tappets of the valves 31 are drawn up and are not in contact with the film.

In FIG. 3b, in contrast, the valves 30 are open, whereas the valves 31 are closed. There is in contrast no difference with respect to the flow paths between the outer connectors 7 for the patient, 9 for the drainage and 10 for the solvent bag. It is thus ensured by an alternating relief of the film by opening the valves that no permanent creep deformation of the film takes place.

Since a thoroughgoing action of the valve tappets on the film is avoided by the alternating movement of the individual valve tappets during the stand-by mode in accordance with the invention, a long waiting period of up to 15 hours between the setting up and the start of the treatment is also possible in the method in accordance with the invention. In addition, in accordance with the invention, a low overpressure in the cassette is furthermore established during the stand-by mode to avoid any contamination.

The patient can set up the treatment machine and put it into stand-by mode with the help of the present invention, for example at some time in the course of the day. For this purpose, a corresponding user guidance of the treatment machine is provided which gives the patient the choice after the setting up of the treatment machine between an immediate start of the treatment and the stand-by mode in accordance with the invention. Further data inputs such as the desired stand-by period (in hours) or the desired end of stand-by (time) can also be made possible. The user guidance advantageously takes place via a touch screen. The control of the treatment machine is advantageously further configured such that it switches automatically into the stand-by mode after the setting up if the treatment is not started after a specific time.

The patient can take part in an evening social life, e.g. in the evening, thanks to the stand-by mode in accordance with the invention and can connect immediately and start the night treatment without any further time-consuming preparation at the start of the night treatment. The treatment can then be carried out automatically during sleep in the known manner as described further above.

A standard treatment such as is also carried out with a treatment machine in accordance with the invention after the stand-by mode, e.g. during the night, will now be described with reference to FIG. 4. Since the device has already been set up, the patient can immediately be connected to the dialysis machine. For this purpose, he removes the protective cap from the patient connector and screws on the catheter extension.

Figure 4:
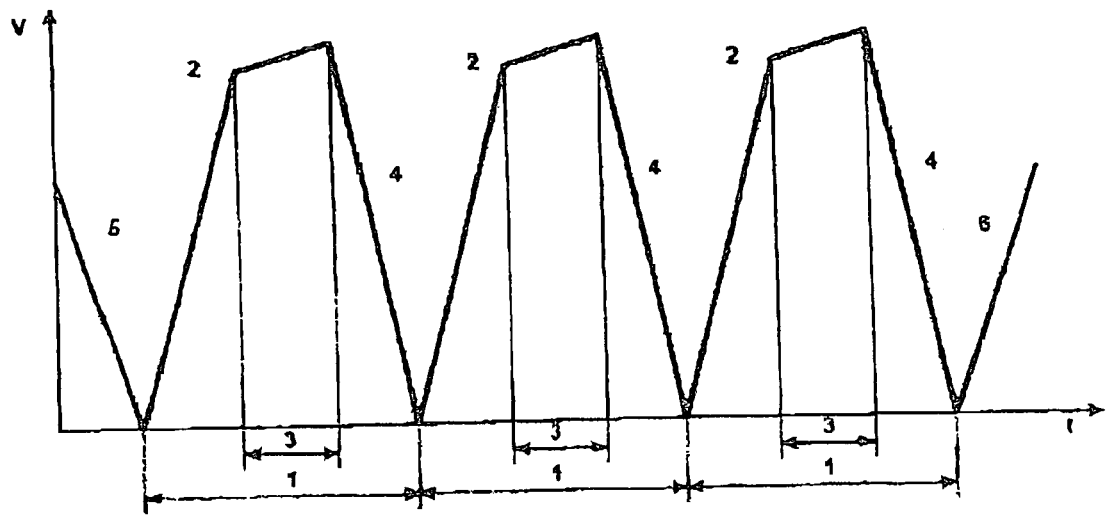
FIG. 4 a standard treatment in peritoneal dialysis.

As shown in FIG. 4, dialysis liquid is now pumped out of the stomach area of the patient in an initial outflow 5. Then fresh liquid is pumped into the stomach area through an inlet 2 and remains there for a certain dwell time 3. The patient is then emptied again with an outflow 4. The sequence of inlet, dwell time and outflow is called a treatment cycle which can be repeated depending on the prescription. The treatment can be ended with a last inflow 6. In the diagram in FIG. 4, the volume V is entered over the time. The initial outflow 5 and the last inflow 6 can optionally be activated by medical staff. After the end of the standard treatment, the patient keeps his dialysis liquid until the next treatment.

In addition to the standard treatment shown in FIG. 4, it is moreover possible in an alternative method to replace the consumed dialysis liquid with fresh dialysis liquid at some time during the day. For this purpose, after the connection of the patient line, the dialysis liquid in the stomach area of the patient is pumped out with an initial outflow 5 and is replaced by fresh liquid which is pumped into the stomach space with a first inflow 2. The treatment method can now be interrupted for a certain time during which the patient disconnects and closes the patient line and the catheter line. The patient can now go about his everyday business until the start of the night treatment. As in the stand-by mode in accordance with the invention between the setup and the first outflow 5, the dialyzer waits for the continuation with a filled set in the time between the first inflow 2 and the start of the night treatment. An overpressure against contamination is therefore maintained in the set in this time. Furthermore, the valves are moved regularly so that no sack formation occurs due to the waiting time.

It is e.g. possible in this alternative method due to the stand-by mode in accordance with the invention between the setting up and the first outflow 5 to set up the treatment unit in the morning and then to put it into the stand-by mode. The time required for the treatment cycle in the day is thus not extended unnecessarily by the setting up required directly before the start of treatment in accordance with the prior art. An enormous flexibilization in his daily agenda thus results for the patient and so a greatly increased quality of life.

The invention claimed is:

1. A method for the preparation of a treatment machine for the treatment of a medical liquid comprising a coupling surface with actuators, with a cassette comprising a hard part with liquid conducting passages which are covered by a flexible film being able to be coupled to the coupling surface of the treatment machine so that the actuators ca control the liquid flow in the liquid conducting passages by pressing the flexible film down into the cassette, comprising the steps of setting up a treatment machine to enable delivery of a medical liquid, switching the treatment machine after the setting up of the treatment machine and before the start of treatment into a stand-by mode, and alternately moving the actuators during the stand-by mode at regular intervals until the treatment is started so as to relieve the flexible film.

2. A method in accordance with claim 1, wherein the stand-by mode can is maintained for 10 hours.

3. A method in accordance with claim 1, wherein the actuators are moved in the stand-by mode so that closed flow paths within the liquid conducting passages remain closed throughout the stand-by mode until the start of treatment.

4. A method in accordance with claim 1, wherein the actuators are moved at regular intervals of 5 to 20 minutes in the stand-by mode.

5. A method in accordance with claim 1, wherein an overpressure is established in the system in the stand-by mode.

6. A treatment machine for the treatment of a medical liquid comprising a coupling surface with actuators and a control, wherein a cassette comprising a hard part with liquid conducting passages which are covered by a flexible film can be coupled to the coupling surface of the treatment machine so that the actuators can control the liquid flow into the liquid conducting passages by pressing the flexible film down into the cassette, wherein said control of the treatment machine has a standby mode which can be activated after the setting up of the treatment machine and before the start of treatment, wherein said actuators are alternately moved during the stand-by mode at regular intervals until the treatment is started so as to relieve the flexible film.

7. A treatment machine in accordance with claim 6, wherein the actuators are moved in the stand-by mode such that closed flow paths within said liquid conducting passages remain closed throughout the stand-by mode until the start of treatment.

8. A treatment machine in accordance with claim 6, wherein the actuators are moved at regular intervals of 5 to 20 minutes in the stand-by mode.

9. A treatment machine in accordance with claim 6, wherein the control establishes an overpressure in the system in the standby mode.

10. A treatment machine in accordance with claim 6, wherein the control automatically switches into the stand-by mode after the setting up if the treatment is not started within a predetermined time.

11. A method or a treatment machine in accordance with claim 1, wherein the treatment machine is a treatment machine for peritoneal dialysis, in particular a treatment machine for automatic peritoneal dialysis.

12. A method for placing a treatment machine for automated peritoneal dialysis (APD) into a stand-by mode between set up and liquid delivery to a patient, said treatment machine having an inserted cassette that includes liquid conducting passages covered by a flexible film, said treatment machine including actuators for controlling liquid flow through the passages by moving the flexible film into and out of the passages to open and close the passages, said method including the steps of setting up the treatment machine and the inserted cassette to enable liquid to reside within passages of the cassette and preventing liquid from delivery to a patient by actuating selective actuators to move the flexible film to a closed position, opening and closing selective actuators at regular intervals to move the flexible film between open and closed positions to prevent the flexible film from permanently deforming into a closed position while maintaining the liquid to remain residing within the passages before delivery to a patient.

13. A treatment machine for automated peritoneal dialysis (APD), including a cassette inserted therein, said cassette including liquid conducting passages covered by a flexible film, said treatment machine including a coupling surface with actuators, said coupling surface coupled to said cassette with said actuators enabling movement of the flexible film into and out of said liquid conducting passages to open and close the liquid conducting passages, said actuators selectively actuated to enable liquid to reside within the passages of the cassette in advance of delivery to a patient, said actuators moving the flexible film into and out of the passages at regular intervals to prevent permanent deformation of the flexible film while enabling the liquid to remain resident within said passages in advance of delivery to a patient.

14. The treatment machine of claim 13, wherein said actuators comprise valve tappets.

* * * * *